US010509011B2

(12) United States Patent
Atkinson et al.

(10) Patent No.: US 10,509,011 B2
(45) Date of Patent: Dec. 17, 2019

(54) ION MOBILITY SPECTROMETER WITH ION MODIFICATION

(71) Applicant: Smiths Detection-Watford Limited, Hertfordshire (GB)

(72) Inventors: Jonathan Atkinson, Herfordshire (GB); Alastair Clark, Hertfordshire (GB)

(73) Assignee: Smiths Detection-Watford Limited (GB)

( * ) Notice: Subject to any disclaimer, the term of this patent is extended or adjusted under 35 U.S.C. 154(b) by 0 days.

(21) Appl. No.: 16/201,494

(22) Filed: Nov. 27, 2018

(65) Prior Publication Data
US 2019/0187095 A1 Jun. 20, 2019

Related U.S. Application Data

(63) Continuation of application No. 15/518,583, filed as application No. PCT/GB2015/053033 on Oct. 14, 2015, now Pat. No. 10,139,367.

(30) Foreign Application Priority Data

Oct. 14, 2014 (GB) ....................... 1418182

(51) Int. Cl.
*G01N 27/62* (2006.01)
*H01J 49/04* (2006.01)
(52) U.S. Cl.
CPC ........ *G01N 27/622* (2013.01); *H01J 49/0422* (2013.01); *H01J 49/0495* (2013.01)
(58) Field of Classification Search
CPC .. H01J 49/00; H01J 49/02; H01J 49/04; H01J 49/0422; G01N 27/622

USPC ................................ 250/281, 282, 288, 289
See application file for complete search history.

(56) References Cited

U.S. PATENT DOCUMENTS

2003/0209665 A1 11/2003 Losch et al.
2006/0071159 A1 4/2006 Hashimoto et al.
2007/0007448 A1* 1/2007 Wang ..................... H01J 49/16
250/288

(Continued)

FOREIGN PATENT DOCUMENTS

| CN | 101688848 A | 3/2010 |
| CN | 101918827 A | 12/2010 |
| CN | 102539514 A | 7/2012 |
| CN | 203405367 U | 1/2014 |

(Continued)

OTHER PUBLICATIONS

Combined Search and Examination Report dated Mar. 30, 2015 for Appln. No. GB1418182.0.

(Continued)

*Primary Examiner* — Jason L McCormack
(74) *Attorney, Agent, or Firm* — Kevin E. West; Advent, LLP

(57) ABSTRACT

Ion modification An ion mobility spectrometer (100) comprising a sample inlet (108) comprising an aperture arranged to allow a sample of gaseous fluid to flow from an ambient pressure region to a low pressure region of the ion mobility spectrometer to be ionised; a controller (200) arranged to control gas pressure in the low pressure region to be lower than ambient pressure; and an ion modifier (126, 127, 202) configured to modify ions in the low pressure region, wherein the ions are obtained from the sample of gas.

16 Claims, 2 Drawing Sheets

(56) References Cited

U.S. PATENT DOCUMENTS

| | | | |
|---|---|---|---|
| 2010/0127166 A1* | 5/2010 | Krueger | G01N 27/622 |
| | | | 250/282 |
| 2010/0200746 A1 | 8/2010 | Osgood et al. | |
| 2011/0114837 A1* | 5/2011 | Li | G01N 27/622 |
| | | | 250/286 |
| 2011/0303024 A1 | 12/2011 | Wallis et al. | |
| 2013/0026357 A1* | 1/2013 | Matthews | G01N 27/622 |
| | | | 250/282 |
| 2013/0092834 A1 | 4/2013 | Covey et al. | |
| 2014/0151546 A1* | 6/2014 | Li | H01J 49/062 |
| | | | 250/282 |
| 2014/0284472 A1* | 9/2014 | Verenchikov | G01N 27/622 |
| | | | 250/282 |
| 2016/0187297 A1* | 6/2016 | Sharp | G01N 27/62 |
| | | | 250/282 |

FOREIGN PATENT DOCUMENTS

| | | |
|---|---|---|
| EP | 1646068 A2 | 4/2006 |
| JP | 2013228211 A | 11/2013 |
| WO | 2008097962 A2 | 8/2008 |
| WO | 2014140577 A1 | 9/2014 |
| WO | 2014146200 A1 | 9/2014 |

OTHER PUBLICATIONS

International Search Report dated Feb. 2, 2016 for PCT/GB2015/053033.

Office Action for Russian Patent Application No. 2017115148/28, dated Apr. 3, 2019.

Office Action for Chinese Patent Application No. 201580056073.5, dated Apr. 18, 2019.

* cited by examiner

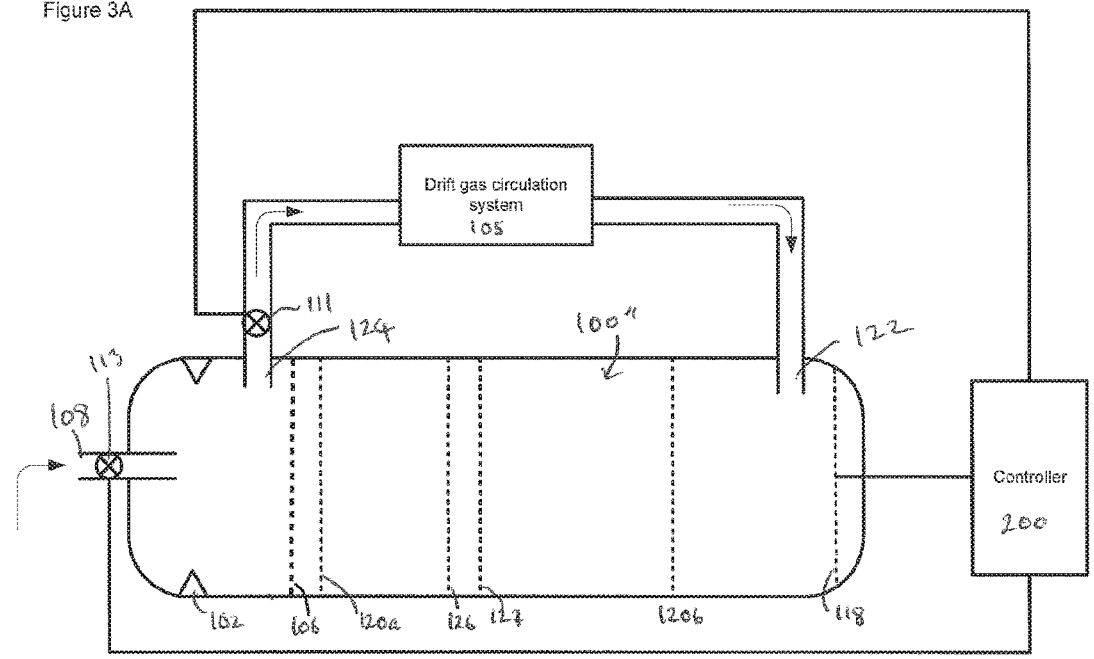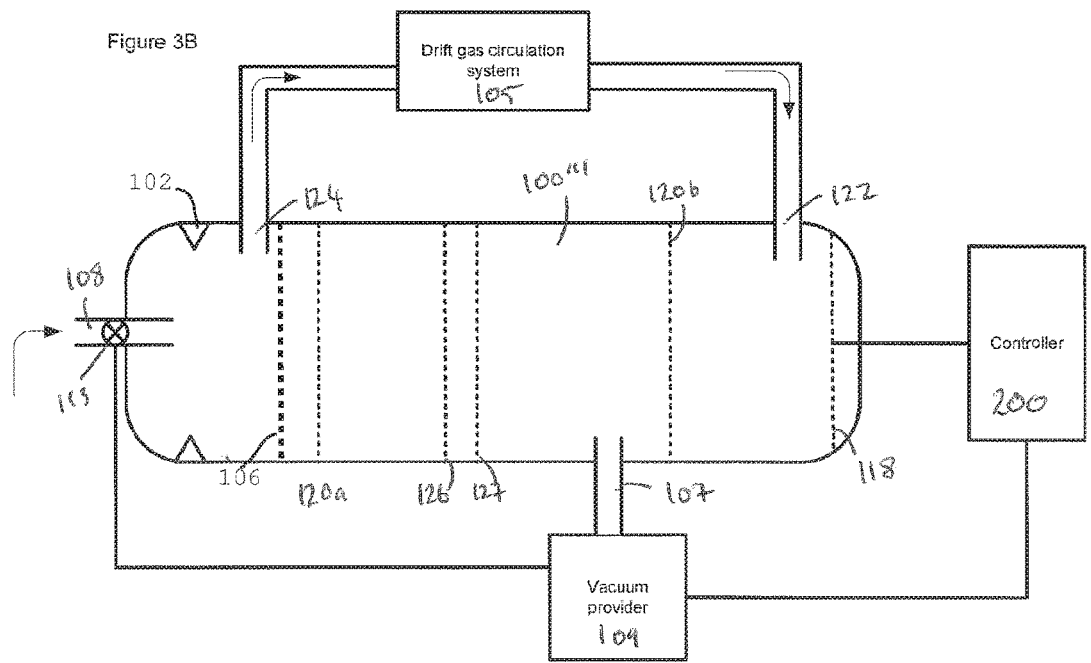

ION MOBILITY SPECTROMETER WITH ION MODIFICATION

FIELD OF THE INVENTION

The present disclosure relates to apparatus and methods, and more particularly to spectrometers, and to spectrometry methods.

BACKGROUND

Ion mobility spectrometers (IMS) can identify material from a sample of interest by ionising material (e.g., molecules, atoms) and measuring the time it takes the resulting ions to travel a known distance through a drift gas under a known electric field. Each ion's time of flight can be measured by a detector, and the time of flight is associated with the ion's mobility. An ion's mobility relates to its mass and geometry. Therefore, by measuring the time of flight of an ion in the detector it is possible to infer an identity for the ion. These times of flight may be displayed graphically or numerically as a plasmagram. Other types of spectrometers, such as mass spectrometers analyse ions according to their mass-charge ratio.

To improve the ability of a spectrometer to identify ions in a sample of interest, it is suggested to modify some of the ions using a radio frequency, RF, electric field (e.g. by fragmenting them) to provide additional information which can be used to infer an identity for the ions. This may improve the ability to resolve differences between ions. Where measurements are performed in the presence of contaminants, or in difficult operating conditions, or where a sample comprises ions with similar geometries and masses etc. ion modification is one way to assist the ion mobility spectrometers ability to detect and identify ions. Ions which are produced by this process of ion modification may be termed "daughter ions", and ions from which daughter ions are produced may be termed "parent ions".

It is desirable to increase the proportion of parent ions that are modified to provide daughter ions, and also to increase the energy efficiency of the on modification process.

BRIEF DESCRIPTION OF DRAWINGS

Embodiments of the disclosure will now be described, by way of example only, with reference to the accompanying drawings, in which:

FIG. 3A shows a second schematic diagram of a spectrometer; and

FIG. 3B shows another schematic diagram of a spectrometer.

In the drawings like reference numerals are used to indicate like elements.

SPECIFIC DESCRIPTION

Figure 1:
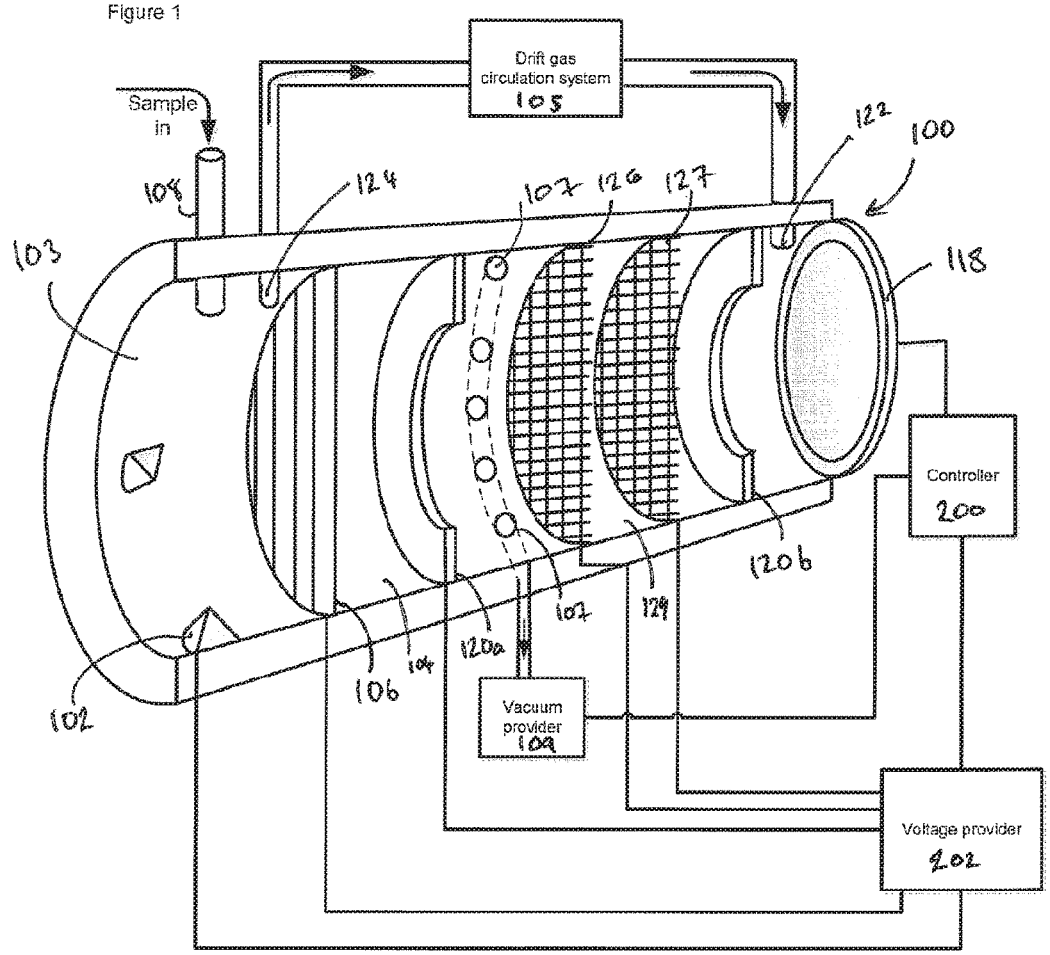
FIG. 1 is an illustration of a part section through a spectrometer.

Aspects of the disclosure relate to the application of energy, such as an alternating electric field and/or heat, to modify ions obtained from a sample of interest. This energy generally raises the effective temperature of the ions and may cause them to undergo more frequent and energetic collisions either with themselves or with molecules of a gas in which they are carried. It has now been found that the proportion of parent ions that are converted to daughter ions can be increased if ion modification is performed at low pressure (e.g. lower than atmospheric pressure).

An aspect of the disclosure provides an ion mobility spectrometer comprising a sample inlet arranged to allow a sample of gas to pass from an ambient pressure region to a low pressure region of the ion mobility spectrometer, and a controller arranged to control gas pressure in the low pressure region to be lower than ambient pressure. The pressure in the low pressure region may be at least 200 mb below ambient pressure, for example between 150 mb below and 800 mb below ambient pressure. An ion modifier is arranged to modify ions in the low pressure region. The sample inlet may comprise an aperture, such as a pinhole inlet, arranged to allow the sample of gas to flow through the inlet. In some other embodiments the sample inlet may comprise a membrane arranged to allow the sample of gas to diffuse through the inlet.

This low pressure region may comprise a drift region of the ion mobility spectrometer or may be provided in an intake stage of a spectrometer. A flow of drift gas may be provided along the drift region towards the sample inlet aperture. The controller may control the flow of drift gas to control the pressure in the low pressure region.

The sample inlet may comprise an aperture which may be controllable to open to obtain a flow of gas entraining a sample through the sample inlet, and also controllable to restrict flow through the sample inlet, for example to obstruct, for example to close the sample inlet. The timing with which the ion modifier is operated to apply energy to modify ions may be selected based on the timing with which the sample inlet is opened and/or closed. For example the ion modifier may be operated so that the application of energy coincides with opening of the sample inlet aperture. The timing of operating the ion modifier may be based on the operation of the sample inlet aperture, for example the two may be synchronised.

The controller may be configured to pump on the low pressure region to reduce the gas pressure in the low pressure region below ambient pressure.

An ion modifier can be arranged between an ioniser and a detector in the path of ions travelling from the ioniser toward the detector. The ion modifier may comprise two electrodes, and the electrodes may be configured so that ions travelling through the region between the two electrodes can be subjected to an alternating electric field aligned with the direction of travel of the ions towards the detector. For example, the electrodes may each comprise a grid of conductors arranged transverse to the direction of travel of the ions towards the detector. These and other possibilities will now be discussed in more detail with reference to the drawings.

FIG. 1 is an illustration of a part section cut away view through such an ion mobility spectrometer (IMS) 100.

The ion mobility spectrometer 100 illustrated in FIG. 1 includes an ioniser 102 that is separated from a drift region 104 by a gate 106. The ioniser may be arranged in an ionisation region 103 into which gas can flow through a sample inlet 108. The gate 106 can control passage of ions from the ioniser 102 and the ionisation region 103 into the drift region 104.

The sample inlet illustrated in FIG. 1 may comprise an aperture 108 such as a pinhole, for example a capillary inlet. The aperture may have a diameter of less than 1 mm, for example having a diameter of less than 0.8 mm, for example at least 0.2 mm, for example at least 0.4 mm, for example about 0.6 mm. The gas flowing through this aperture may carry a sample of a substance to be ionised by the ioniser 102.

In the example illustrated in FIG. 1, the drift region 104 lies between the ioniser 102 and a detector 118, so that ions can reach the detector 118 by traversing the drift region 104. The drift region 104 may comprise a series of drift electrodes 120a, 120b for applying a voltage profile along the drift region 104 to move ions from the ioniser 102 along the drift region 104 toward the detector 118.

The IMS 100 may be configured to provide a flow of drift gas in a direction generally opposite an ion's path of travel to the detector 118. For example, the drift gas can flow from adjacent the detector 118 toward the gate 106. As illustrated, a drift gas inlet 122 and drift gas outlet 124 can be used to pass drift gas through the drift region 104. A drift gas circulation system 105 is adapted to move a flow of drift gas through the drift region 104 from the drift gas inlet 122 to the drift gas outlet 124, and may be configured to recirculate this drift gas, and for example to filter and clean drift gas removed via the drift gas outlet before it is recirculated to the drift gas inlet 122 to pass back through the drift region 104.

The vacuum provider 109 may be controlled by the controller 200. The vacuum provider 109 may control the pressure of gas in a low pressure region of the IMS to be less than ambient pressure, for example to be 200 mb below ambient pressure or lower, for example 300 mb below or lower, for example 400 mb below or lower. These low pressures, 200 mb below and lower may be of particular utility in examples where the inlet comprises a membrane. The low pressure region may comprise the ionisation region 103, and in some examples a reaction region, and/or the drift region 104.

The low pressure region of the IMS may comprise vents 107, which may be arranged in a wall of the drift region 104, and coupled to a vacuum provider 109 such as a pump arranged to pump on the low pressure region of the IMS to reduce the gas pressure in this region. The vents 107 may be arranged in positions in the wall of the drift region 104 selected to reduce disturbance of the flow of drift gas along the drift region 104. For example, the vents 107 may be evenly (perhaps symmetrically) distributed around the perimeter of the drift region 104, for example the vents may be distributed around the circumference of the drift region 104.

However it is achieved, the controller 200 may be configured to provide a gas pressure in this region of less than 150 mb below ambient pressure, for example at least 200 mb below, in some embodiments less than 300 mb below ambient pressure, in some embodiments the gas pressure in this region is 500 mb below ambient pressure. In some embodiments the gas pressure is above 800 mb below ambient pressure, for example above 700 mb below ambient pressure, for example above 600 mb below ambient pressure. For example the pressure may be between 150 mb and 800 mb below ambient pressure.

An ion modifier is arranged to apply energy to modify ions in the low pressure region of the ion mobility spectrometer. In the example illustrated in FIG. 1 the ion modifier comprises electrodes 126, 127 configured to apply energy by subjecting ions to an alternating electric field.

The ion modifier electrodes 126, 127 can be spaced apart from the gate electrode 106.

As illustrated, the ion modifier electrodes 126, 127 are arranged in the drift region 104, between the gate electrode and the detector. In an embodiment the ion modifier may be arranged in the ionisation region 103, for example between the inlet 108 and the gate 106.

Each of the ion modifier electrodes 126, 127 can comprise an array of conductors, such as a grid, arranged across the drift region 104. As illustrated, the conductors of each ion modifier electrode 126, 127 may have gaps between them such that ions can pass through each electrode by travelling through the gaps. In one example ions pass through the gaps between the conductors of the electrode 126, into a region 129 between the electrodes 126, 127, and out of the region through the gaps between the conductors of the electrode 127. While the ions are in the region between the electrodes 126, 127 they can be subjected to an alternating, RF, electric field. The field may be aligned with the direction of travel of the ions towards the detector. It will be appreciated in the context of the present disclosure that this alignment need not be perfect or uniform. The ion modifier can be operated in a first mode in which ions passing through the ion modifier are subjected to an alternating electric field to modify the ions, and in a second mode in which the amplitude of the alternating electric field is lower, for example where it is switched off, to allow ions to pass through the ion modifier without being modified.

The detector 118 may be coupled to provide a signal to a controller 200. Current flow from the detector 118 can be used by the controller 200 to infer that ions have reached the detector 118, and a characteristic of the ions can be determined based on the time for ions to pass from the gate 106 along the drift region 104 to the detector 118. Examples of a detector 118 are configured to provide a signal indicating that ions have arrived at the detector 118. The detector may comprise a conductive electrode (such as a Faraday plate).

The drift electrodes 120a, 120b, may be arranged to guide ions toward the detector 118, for example the drift electrodes 120a, 120b may comprise rings which may be arranged around the drift region 104 to move ions towards the detector 118. Although the example of FIG. 1 includes only two drift electrodes 120a, 120b, in some examples a plurality of electrodes may be used, or a single electrode may be used in combination with the detector 118 to apply an electric field to guide ions toward the detector 118. As shown in FIG. 1 a voltage provider 202 is coupled to be controlled by the controller 200. The voltage provider 202 may also be coupled to provide voltages to the ioniser 102 to enable material from a sample to be ionised. In an embodiment the voltage provider 202 is coupled to the gate electrode 106 to control the passage of ions from the ionisation region 103 into the drift region 104.

The voltage provider 202 can be coupled to the drift electrodes 120a, 120b for providing a voltage profile for moving ions from the ioniser 102 toward the detector 118. As illustrated in FIG. 1, the voltage provider 202 may be coupled to provide a time varying, for example alternating, RF voltage to the ion modifier electrodes 126, 127. By controlling the voltage of one or both of the two ion modifier electrodes 126, 127, with respect to the other, the voltage provider can provide a time varying voltage between the first electrode and the second electrode. Controlling the voltage of the ion modifier electrodes may comprise controlling the phase of the voltage applied to one or both electrodes 126, 127. For example the voltage of both electrodes may be varied and there may be a phase difference between the voltages applied to each electrode, for example the voltages maybe in anti-phase.

As will be appreciated, the controller 200 may control operation of the pump to select the pressure in the low pressure region of the IMS. The inflow and outflow of gas to and from this region, e.g. gas flow through the sample inlet aperture 108 and the drift gas inlet 122, may then be selected to maintain this pressure whilst providing the desired flows of gas. For example the inlet aperture 108 may comprise an actuator (such as a piezo-driven diaphragm), selectively operable to draw gaseous fluid into the ionisation region 103, and operation of the vacuum provider may be selected to balance pressure changes associated with samples being drawn into the ionisation region through the aperture. The flow of drift gas along the drift region 104 can then be provided in addition to any flow from the aperture, and the operation of the vacuum provider 109 may be adjusted to account for it. This is just one possibility, and other approaches may be used—for example pressure control may be provided by controlling one or more of the inflows and outflows of gas to and from the low pressure region of the IMS, e.g. gas flow through the sample inlet aperture 108, the drift gas inlet 122, and the drift gas outlet 124. For example the actuator may comprise a controllable stopper such as a shutter that is controllable to inhibit, for example to prevent, flow of gaseous fluid through the aperture.

In some embodiments the inlet 108 may comprise a membrane inlet adapted to allow sample vapour to permeate, for example to diffuse through, the membrane into the low pressure region.

Figure 2:
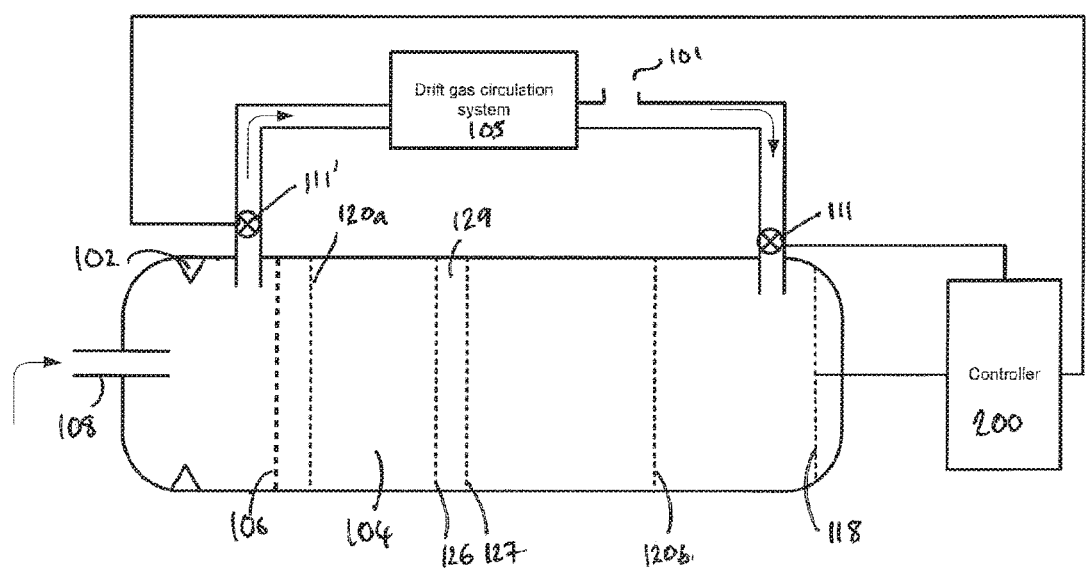
FIG. 2 shows a schematic diagram of a spectrometer.

FIG. 2 illustrates a schematic view of an ion mobility spectrometer 100'. In the interests of clarity the voltage provider and its connections to the various electrodes are not shown in FIG. 2.

The ion mobility spectrometer 100' illustrated in FIG. 2 comprises an open sample inlet aperture 108, for example a pinhole or capillary inlet. The flow of gas through this aperture is determined by the area of its cross section through which gas can flow, and by its length. The sample inlet aperture may comprise a membrane.

In the example illustrated in FIG. 2, the controller is coupled to control the circulation of drift gas, for example to control the inflow of gas in to and/or outflow out from the drift region 104 via the drift gas inlet and outlet. This may be achieved by control of the drift gas circulation system 105, or by control of the rate at which drift gas is introduced into the drift region 104 through the drift gas inlet, and/or the rate at which drift gas leaves the drift region 104 through the drift gas outlet.

The drift gas circulation system 105 may be referenced to ambient pressure, for example the output of the drift gas system 105 may be referenced to ambient pressure, for example by a vent 101. The drift gas inlet may comprise a restrictor 111, such as a tap-like variable constriction, for example a controllable valve, and the controller may be configured to control this restrictor 111 to regulate the relative inflow and outflow of drift pas from the drift region 104. In this way the pressure in the low pressure region of the IMS 100' may be regulated to be less than ambient pressure, and the ion modifier 126, 127 can apply energy to modify ions in this low pressure region.

FIG. 3A and FIG. 3B illustrate possibilities in which the sample inlet aperture 108 may comprise a restrictor 113 that is operable to be closed to inhibit flow of gas through the sample inlet aperture 108, and operable to be opened to allow a stream of gas to flow through the sample inlet aperture 108. The controller 200 illustrated in FIG. 3A and FIG. 3B is operable to control the sample inlet restrictor 113 to control the flow of gas through the sample inlet aperture 108. The controller 200 may operate this restrictor 113 to obtain a sample of gas entraining a sample to be ionised, and also to control, e.g. to regulate, pressure in the low pressure regions of the IMS 100", 100'''.

The apparatus illustrated in FIG. 3A need not include the vent 101 to reference the drift gas system 105 to ambient pressure but is otherwise similar to that illustrated in FIG. 2 and the controller 200 of FIG. 3A may be configured to control the relative rate of drift gas inflow and outflow using a controllable restrictor 111 arranged to restrict one or both of the drift gas inlet 122, and the drift gas outlet 124, or by controlling the drift gas circulation system 105.

In the example illustrated in FIG. 3B, an IMS 100''' comprises a vacuum provider 109 such as a pump configured to operate as the vacuum provider 109 explained above with reference to FIG. 1. As in the example illustrated in FIG. 3A, the controller 200 of this IMS 100" is configured to control pressure in the low pressure regions of the IMS by controlling the vacuum provider 109 and the rate at which drift gas is introduced into the drift region 104 through the sample inlet aperture 108. For example the controller 200 may control operation of the restrictor 113 to control the flow of gas through the sample inlet aperture 108.

In these and other embodiments of the disclosure a pressure sensor may be provided for sensing pressure in the low pressure regions of the IMS, and the controller 200 may be configured to control the pressure based on this sensed pressure. In some embodiments the relative inflow/outflow rates provided by the vacuum provider and/or drift gas inlet/outlet, and/or sample inlet aperture 108 can be predetermined based on a calibration and/or selected based on ambient pressure to provide the desired pressure in the low pressure regions of the IMS.

The time varying voltage applied to the ion modifier may have a frequency of at least 2.5 MHz. In an embodiment the frequency is at least 3 MHz, or at least 5 MHz, in some embodiments at least 6 MHz. In an embodiment the frequency is less than 100 MHz, in some embodiments the frequency is less than 50 MHz, in some embodiments less than 20 MHz, in some embodiments less than 15 MHz, or less than 10 MHz. For example, the frequency may be between 3 MHz and 20 MHz, or between 6 MHz and 12 MHz. In some examples the frequency is about 8 MHz.

In an embodiment the voltage provider is configured to control the voltage of the first electrode to vary less than the voltage of the second electrode. In an example, the amplitude of the variation of the voltage of one of the ion modifier electrodes 126, 127 may be less than the amplitude of the variation of the other ion modifier electrode. For example, the voltage provider 202 may control the voltage of one of the ion modifier electrodes 126, 127 based on a direct current, DC, reference voltage so that the voltage of one electrode is constant whilst the other varies. In one example the voltage provider may control the voltage of the ion modifier electrodes 126, 127 so the variation of each is sinusoidal, or a square wave, a saw tooth, or a train of pulses, and the amplitude of the variation in voltage at one ion modifier electrode may be less than the variation in voltage at the other ion modifier electrode. In embodiments, applying asymmetric voltages to the ion modifier electrodes 126, 127 may reduce unwanted coupling of RF electric fields with other components of the spectrometer, and this may reduce unwanted leakage of electromagnetic interference from the spectrometer.

The voltage provider 202 may control the voltage of the two ion modifier electrodes 126, 127 to vary with a selected phase difference, for example the voltage controller may control the voltage of the two ion modifier electrodes 126, 127 so that the positive voltage excursion of one electrode occurs during the negative voltage excursion of the other. For example, the voltage provider 202 may control the voltage of the two ion modifier electrodes 126, 127 to vary in anti-phase. The voltage excursions of the two electrodes may be of the same amplitude.

In some examples the voltage provider may control the voltage of one of the ion modifier electrodes 126, 127 to vary more quickly than the voltage of the other ion modifier electrode 126, 127. For example, one of the ion modifier electrodes 126, 127 maybe coupled to a reference voltage, which may comprise a DC voltage, whilst the other ion modifier electrode may be coupled to an alternating voltage, such as an RF voltage.

As noted above, the drift electrodes 120a, 120b may provide a voltage profile that moves ions along the drift region 104 so that the ions travel from the ioniser toward the detector. As illustrated in FIG. 1 the first ion modifier electrode 126 and the second ion modifier electrode 127 can be spaced apart in the direction of travel of the ions. In an embodiment, the voltage provider is configured to control the voltage of at least one of the ion modifier electrodes 126, 127 based on the location of the ion modifier electrodes 126, 127 along the drift region 104 and based on the voltage profile provided by the drift electrodes 120a, 120b. In an embodiment the time average of the voltage of the ion modifier electrodes 126, 127 is selected based on this voltage profile. In an embodiment the voltage provider 202 provides a DC voltage offset between the ion modifier electrodes 126, 127. This DC voltage offset may be based on the spacing between the ion modifier electrodes 126, 127 and the voltage profile.

As shown in FIG. 1 the ion modifier electrodes 126, 127 each comprise a grid of conductors. The ion modifier electrodes 126, 127 may be parallel to each other. In an embodiment the grids are arranged across (e.g. transverse, for example perpendicular to) the direction of travel of ions from the ioniser towards the detector.

Ions travelling towards the detector can pass through gaps between the conductors of one of the ion modifier electrodes 126, and into the region 129 between the ion modifier electrodes 126, 127 where they can be subjected to a radio frequency, RF, electric field.

The ion modifier electrode 127 that is closer to the detector 118 may be arranged so that the conductors of that electrode 127 lie in the path of ions travelling through the gaps in the other ion modifier electrode. The conductors 127 of one electrode may at least partially obstruct the gaps in the other electrode 126. It has been found that this may increase the number of parent ions that are converted into daughter ions by the ion modifier. The conductors of the electrode 126 are shown as being parallel to the conductors of the electrode 127. In an embodiment, the electrodes 126, 127 may be arranged in parallel planes, but the conductors of the two electrodes 126, 127 may be angularly offset from one another (e.g. misaligned), so that the conductors of one ion modifier electrode lie in the path of ions travelling through the gaps in the other ion modifier electrode. In an embodiment, the electrodes 126, 127 may be arranged in parallel planes, but the conductors of the two electrodes 126, 127 may be laterally offset from one another, in a direction transverse to the direction of travel of the ions, so that the conductors of one ion modifier electrode 126 lie in the path of ions travelling through the gaps in the other ion modifier electrode 127. In some embodiments these features are combined so that the conductors of the two ion modifier electrodes 126, 127 are both laterally and angularly offset.

In some embodiments the present disclosure provides an intake stage apparatus for the intake of a sample to a spectrometer. The intake stage may comprise a low pressure region having a pressure lower than 200 mb less than ambient pressure, for example lower than 300 mb below, for example lower than 400 mb below. In some embodiments the gas pressure in this low pressure region is 500 mb below ambient pressure. In some embodiments the gas pressure is above 800 mb below ambient pressure, for example above 700 mb below ambient pressure, for example above 600 mb below ambient pressure. For example the pressure may be between 150 mb and 800 mb below ambient pressure. The low pressure region may comprise an inlet for obtaining a sample of gaseous fluid, an ioniser for obtaining parent ions from the sample, and an ion modifier configured to modify the parent ions in the low pressure region to provide daughter ions. The ion modifier may have any of the features of any of the ion modifiers described herein, and in particular the features of the electrodes described in the preceding paragraphs. This intake stage may comprise an outlet arranged for providing the daughter ions to the spectrometer for analysis.

In an embodiment the IMS and the voltage provider may be contained in a common housing. In an embodiment the ion modifier electrodes 126, 127 may be disposed in the drift region 104. The ion modifier electrode may be spaced along the drift region 104 from the gate electrode. The spacing may be at least 0.5 mm from the gate electrode 106, for example at least 2 mm, in an embodiment at least 4 mm, in an embodiment at least 6 mm, or at least 7 mm. In an embodiment the spacing may be less than 150 mm, or less than 100 mm, for example less than 50 mm.

The ion modifier electrodes 126, 127 may comprise a grid such as a wire mesh. The mesh may be a lattice of conductors which may be arranged in a repeating square pattern. The conductors may have a thickness of at least 10 µm, for example less than 30 µm. The pitch of the mesh may be at least 200 µm, for example less than 500 µm. The two meshes may be separated from one another by at least 0.1 mm, for example at least 0.15 mm, for example less than 0.4 mm, for example less than 0.3 mm.

In one embodiment the nearest electrode 126 is arranged in the drift region 104 7 mm from the gate 106. In this embodiment the spacing between the ion modifier electrodes 126, 127 is 0.2 mm, and the electrodes comprise a mesh having a square pattern. In this embodiment the conductors of the mesh have a thickness of 21 µm and are arranged on a 363 µm pitch. The conductors may comprise wire.

Without wishing to be bound by theory it is believed that, at a frequency of 1.9 MHz, the distance that an ion travels in one half of the RF waveform is comparable to the distance between the two modifier electrodes 126, 127. As such, the ions do not experience as many cycles of the RF as they do when the frequency is increased. Put another way, if an ion has a velocity of 1000 metres per second then in one half of a 2 MHz cycle it will travel 0.25 mm if the applied voltage is a square wave, or 0.176 mm if the applied voltage is a sine wave. If the gap between the ion modifier electrodes 126, 127 is 0.25 mm or perhaps less it can be seen that, after only a few cycles the ion will be ejected from the ion modifier. When the frequency is increased, for example to 6 MHz, or to 8 MHz, the distance travelled in one half of a cycle reduces (e.g. becomes 0.044 mm at 8 MHz). Therefore the ion can experience many cycles before it leaves the modifier, and the probability of it experiencing a collision with high enough energy for a bond to break or some other molecular transformation to take place can be increased.

In some embodiments even higher frequencies, for example between 8 MHz and 10 MHz may reduce ion losses in the ion modifier—again without wishing to be bound by theory, this may be because the ions are able to get closer to the conductors of the ion modifier electrodes before they reach a "point of no return" (where they will be drawn onto the conductors). As such fewer ions may hit the wires and more therefore survive the journey through the modifier further increasing sensitivity.

It will be appreciated that in the context of the present disclosure that RF electric fields comprise any alternating electric field having frequency characteristics appropriate for applying energy to modify ions (e.g. by imparting energy to them to raise their effective temperature).

Other examples and variations will be apparent to the skilled reader in the context of the present disclosure.

Embodiments of the disclosure comprise methods and apparatus for ionisation of samples, for example samples of gaseous fluids such as gases, vapours, and aerosols. Example drift gases include, but are not limited to, nitrogen, helium, air, air that is recirculated (e.g., air that is cleaned and/or dried) and so forth by the drift gas circulation system. Drift gases need not be used, some examples of the disclosure may be used in systems where the mean free path of ions is comparable to, for example greater than or equal to, the length of the drift chamber. Rather than mobility, these examples of the disclosure may measure the mass to charge ratio of the ions for example based on a time of flight measurement or based on subjecting ions to a magnetic field to deflect them from their direction of travel.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide computer program products such as machine readable instructions and/or tangible, non-transitory storage media comprising program instructions operable to program a processor to perform any one or more of the methods described and/or claimed herein and/or to provide data processing apparatus as described and/or claimed herein.

The uses and operations of the apparatus described herein are intended also as a disclosure of the method, and the particular structure of the apparatus may not be relevant—therefore features of apparatus embodiments may be combined with the method embodiments described and claimed herein. Likewise, the methods described herein may be implemented by suitable configuration of the apparatus disclosed herein.

The activities and apparatus outlined herein may be implemented using controllers and/or processors which may be provided by fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

Where reference is made to electrodes it will be appreciated that any arrangement of conductors may be used, for example electrodes may comprise metals or other conductors and may be at least partially exposed and/or partially insulated. The voltage providers described herein may comprise an AC power supply, which may comprise one or more step-up or step down transformers, the voltage providers may also comprise DC power supplies such as batteries or fuel cells or capacitive power stores. Combinations of AC and DC power may be used and the voltage provider may comprise an inverter for providing an AC voltage based on a DC power supply. In some embodiments the voltage provider may comprise rectifiers for providing DC voltage based on an AC power supply. Any combination of AC and DC power supply and voltage providing components may be used. In some embodiments the voltage provider may also operate as a current source.

The invention claimed is:

1. An ion mobility spectrometer comprising:
    a sample inlet comprising a membrane inlet arranged to allow a sample of gaseous fluid to pass from an ambient pressure region to a low pressure region of the ion mobility spectrometer to be ionised;
    an ioniser disposed in the low pressure region of the ion mobility spectrometer and configured to ionise the sample;
    an ion modifier configured to modify ions in the low pressure region, wherein the ions are obtained from the sample of gaseous fluid, wherein the ion modifier comprises two electrodes spaced apart in the direction of movement of the ions towards the detector;
    a controller arranged to control gas pressure in the low pressure region to be lower than ambient pressure by at least 200 mb, wherein the controller is configured to control the ion modifier in a first mode to subject ions to an alternating electric field to modify the ions as they pass through the ion modifier, and to control the ion modifier in a second mode to allow ions to pass through the ion modifier; and
    a detector configured to measure a time of flight associated with the ions travelling from the ioniser, wherein the detector is configured to provide a signal to the controller indicating arrival of ions.

2. The ion mobility spectrometer of claim 1, wherein the controller is arranged to control gas pressure in the low pressure region to be lower than ambient pressure by at least 300 mb.

3. The ion mobility spectrometer of claim 1, wherein the low pressure region comprises a drift region and a drift gas flow provider arranged to provide a flow of drift gas along the drift region towards the sample inlet.

4. The ion mobility spectrometer of claim 3, wherein the drift region is arranged to move ions against the flow of drift gas towards a detector, and the ion modifier is arranged to subject the ions to a radio frequency, RF, electric field aligned with the direction of movement of the ions towards the detector.

5. The ion mobility spectrometer of claim 1, wherein each of the two electrodes comprise a grid of conductors.

6. The ion mobility spectrometer of claim 3, wherein the controller is arranged to control at least one of the flow of drift gas or a flow of gas through the sample inlet to control pressure in the low pressure region.

7. The ion mobility spectrometer of claim 1, further comprising a vacuum provider configured to reduce the gas pressure in the low pressure region.

8. The ion mobility spectrometer of claim 7, wherein the controller is configured to control at least one of: an aperture or the vacuum provider to control pressure in the low pressure region.

9. The ion mobility spectrometer of claim 1, wherein the controller is configured to control timing of operation of the ion modifier based on timing of operation of an ion gate.

10. The ion mobility spectrometer of claim 1 in which the controller is configured to reduce the pressure in the low pressure region in to a range of 200 mbar to 800 mbar.

11. A method for operating an ion mobility spectrometer comprising:
    sampling a gaseous fluid by causing a sample of the gaseous fluid to pass through a sample inlet comprising a membrane inlet from an ambient pressure region to a low pressure region of the ion mobility spectrometer;
    ionising the sample in the low pressure region using an ioniser to provide sample ions, wherein the pressure in the low pressure region is controlled to be lower than ambient pressure by at least 200 mb;
    modifying the sample ions in the low pressure region by using an ion modifier to subject the ions to an alternating electric field to provide modified sample ions for detection, wherein the ion modifier comprises two electrodes spaced apart in the direction of movement of the ions towards a detector, and wherein the pressure in the low pressure region and operation of the ion modifier is controlled by a controller; and
    measuring a time of flight associated with the ions travelling from the ioniser to the detector by providing a signal from the detector to the controller indicating arrival of ions.

12. The method of claim 11, wherein gas pressure in the low pressure region is controlled to be lower than ambient pressure by at least 300 mb.

13. The method of claim 11, wherein modifying the sample ions comprises subjecting the ions to a Radio Frequency (RF) electric field aligned with the direction of movement of the ions.

14. An ion mobility spectrometer comprising:
    a sample inlet comprising a membrane inlet arranged to allow a sample of gaseous fluid to pass from an ambient pressure region to a low pressure region of the ion mobility spectrometer to be ionised;
    a controller arranged to control gas pressure in the low pressure region to be lower than ambient pressure by at least 200 mb; and
    an ion modifier comprising two electrodes spaced apart in the direction of movement of ions towards a detector, the ion modifier electrodes each comprising an array of conductors arranged across the direction of movement of the ions, the ion modifier configured to modify ions in the low pressure region, wherein the ions are obtained from the sample of gaseous fluid;
    wherein the controller is configured to control the ion modifier in a first mode to subject ions to an alternating electric field to modify the ions as they pass through the ion modifier, and to control the ion modifier in a second mode to allow ions to pass through the ion modifier without modifying the ions.

15. The ion mobility spectrometer of claim 14, further comprising an ioniser disposed in the low pressure region of the ion mobility spectrometer and configured to ionise the sample.

16. The ion mobility spectrometer of claim 14, further comprising the detector, wherein the detector is configured to measure a time of flight associated with the ions travelling from the ioniser and to provide a signal to the controller indicating arrival of ions.

* * * * *